United States Patent [19]

Hoelderich et al.

[11] Patent Number: 5,130,435

[45] Date of Patent: * Jul. 14, 1992

[54] PREPARATION OF VINYL ETHERS

[75] Inventors: Wolfgang Hoelderich, Frankenthal; Norbert Goetz, Worms; Leopold Hupfer, Friedelsheim, all of Fed. Rep. of Germany

[73] Assignee: BASF Aktiengesellschaft, Ludwigshafen, Fed. Rep. of Germany

[*] Notice: The portion of the term of this patent subsequent to Oct. 2, 2007 has been disclaimed.

[21] Appl. No.: 565,180

[22] Filed: Aug. 9, 1990

Related U.S. Application Data

[63] Continuation of Ser. No. 309,090, Feb. 10, 1989, abandoned.

[30] Foreign Application Priority Data

Feb. 11, 1988 [DE] Fed. Rep. of Germany ....... 3804162

[51] Int. Cl.$^5$ ............................................. C07D 401/00
[52] U.S. Cl. ................................... 546/256; 546/259; 546/266; 546/283; 546/284; 546/290; 546/303; 546/339; 546/343; 549/14; 549/59; 549/60; 549/62; 549/78; 549/497; 568/579; 568/631; 568/640; 568/647; 568/658; 568/661; 568/664; 568/662; 568/691
[58] Field of Search .............. 568/591, 579, 626, 663, 568/667, 686, 640, 631, 692, 658, 661, 664; 546/256, 259, 266, 283, 284, 290, 303, 339, 343; 549/14, 59, 60, 62, 78, 497

[56] References Cited

U.S. PATENT DOCUMENTS

| 3,705,924 | 12/1972 | Smith et al. | |
|---|---|---|---|
| 4,310,440 | 1/1982 | Wilson et al. | |
| 4,440,871 | 4/1984 | Lok et al. | |
| 4,473,663 | 9/1984 | Patton et al. | 502/208 |
| 4,960,954 | 10/1990 | Hoelderich et al. | 568/691 |

FOREIGN PATENT DOCUMENTS 039410 4/1987 European Pat. Off. .
84507 7/1975 Japan .
2091259 7/1982 United Kingdom .

OTHER PUBLICATIONS

Chemical Abstract, "The Catalytic Decomposition of Acetals by Metallic Oxides", vol. 24, No. 15 (Aug. 10, 1930).

Primary Examiner—Bruce Gray
Attorney, Agent, or Firm—Keil & Weinkauf

[57] ABSTRACT

Vinyl ethers of the formula

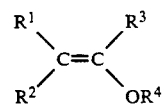

wherein $R^1$, $R^2$ and $R^3$ are identical to or different from one another, each being hydrogen, straight-chain or branched alkyl or alkenyl of up to 12 carbon atoms, cycloalkyl or cycloalkylene of from 5 to 8 carbon atoms, aryl, alkylaryl, alkenylaryl, aralkyl and aralkenyl of from 6 to 16 carbon atoms, halogen-substituted aryl or heterocyclyl, and in addition the radicals $R^1$ and $R^2$ or $R^1$ and $R^3$, together with the carbon atom to which they are bonded, can form a cycloalkane, cycloalkene or a heterocycle, and $R^4$ is alkyl, alkylaryl or aralkyl, are prepared by eliminating an alcohol from an acetal/ketal of the formula

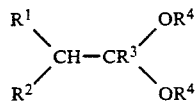

where $R^1$, $R^2$, $R^3$ and $R^4$ are each as defined above, in the presence of a phosphate of zeolite structure and/or a precipitated phosphate of the elements B, Zr, Ce or Fe and/or phosphoric acid or boric acid on carrier material and/or acidic undoped metal oxide as catalyst, the reaction being preferably carried out in the gas phase.

4 Claims, No Drawings

PREPARATION OF VINYL ETHERS

This application is a continuation of application Ser. No. 309,090, filed on Feb. 10, 1989 now abandoned.

The present invention relates to a process for preparing vinyl ethers by eliminating alcohols from acetals/ketals in the presence of heterogeneous catalysts.

Vinyl ethers are used for the preparation of specific homopolymers and copolymers used in paint and adhesive making and as assistants in the textile and leather industry. Furthermore, vinyl ethers are useful intermediates for organic syntheses, for example for Diels-Alder reactions or for the preparation of glutardialdehydes, γ-pyran, γ-picoline and also active substances.

In industry, vinyl ethers are prepared by the Reppe method from acetylene and alcohols in the liquid phase with potassium hydroxide as catalyst. However, since acetylene starting materials are not universally available, an alternative synthesis for vinyl ethers is desirable.

Another method of preparing vinyl ethers comprises the elimination of alcohols from acetals/ketals. It is known that alkali metal phosphates (U.S. Pat. No. 3,705,924), alkaline earth metal phosphates and ammonium phosphates on a carrier material catalyze the conversion.

It is further known to use sulfates such as $NaHSO_4$, sulfates of alkaline earth metals and heavy metals or alkali metal/alkaline earth metal carbonates or CaO (GB 2,091,259) on a carrier material as catalysts.

These catalysts are of the basic type, or the acidity of the carrier material used is much reduced.

We have found that in the preparation of vinyl ethers of the formula (I)

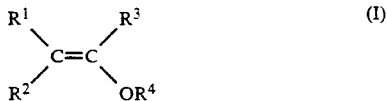

(I)

where $R^1$, $R^2$ and $R^3$ are identical to or different from one another, each being hydrogen, straight-chain or branched alkyl or alkenyl of up to 12 carbon atoms, cycloalkyl or cycloalkylene of from 5 to 8 carbon atoms, aryl, alkylaryl, alkenylaryl, aralkyl and aralkenyl of from 6 to 16 carbon atoms, halogen-substituted aryl or heterocyclyl, and in addition the radicals $R^1$ and $R^2$ or $R^1$ and $R^3$, together with the carbon atom to which they are bonded, can form a cycloalkane, cycloalkene or a heterocycle, and $R^4$ is alkyl, alkylaryl or aralkyl, good results are obtained on eliminating alcohols from acetals/ketals of the formula (II)

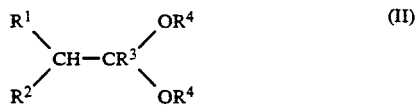

(II)

where $R^1$, $R^2$, $R^3$ and $R^4$ are each as defined above, in the presence of phosphates of zeolite structure and/or precipitated phosphates of the elements B, Zr, Ce or Fe and/or phosphoric acid or boric acid on carrier material and/or acidic undoped metal oxides as catalysts.

Possible $R^1$ to $R^3$ are independently of $R^4$ hydrogen and straight-chain or branched alkyl of from 1 to 12, in particular of from 1 to 8, preferably of from 1 to 4, carbon atoms.

This means that surprisingly and contrary to the prior art even acidic catalysts or carrier materials without doping are very highly suitable for the reaction.

Suitable alkyl or alkenyl is for example methyl, ethyl, n-propyl, i-propyl, propenyl, i-propenyl, n-butyl, i-butyl, n-butenyl, i-butenyl, pentyl, pentenyl, hexyl, hexenyl, heptyl, heptenyl, octyl, octenyl, nonyl, nonenyl, decyl, decenyl, dodecyl or dodecenyl.

Cycloalkyl is for example cyclopentyl, cyclohexyl, cycloheptyl, cyclopentenyl or cyclohexenyl.

Suitable aromatic radicals are for example phenyl, benzyl, 2-phenylethyl, 3-phenylpropyl, 2-phenylpropyl, 4-phenylbutyl, 3-phenylbutyl, 2-phenylbutyl or 3-phenylbutenyl, which may each be additionally substituted by radicals which are inert under the reaction conditions such as alkyl or halogen.

Heterocyclic and heteroaromatic radicals are for example tetrahydrofuran, dihydrofuran, furan, tetrahydrothiophene (thiophane), dihydrothiophene, thiophene, pyridine and thiopyran radicals. These radicals may additionally be substituted by radicals which are inert under the reaction conditions, such as alkyl or halogen.

$R^4$ is for example alkyl such as methyl, ethyl, n-/i-propyl, propenyl, n-, i-, t-butyl, butenyl, octyl or octenyl or aralkyl such as benzyl, phenylethyl or phenylpropyl or alkylaryl such as toluyl or xylyl.

Acetals of saturated aliphatic aldehydes, for example acetaldehyde, propionaldehyde, butyraldehyde, pentanal, hexanal and higher homologous n-alkanals such as octanals and decanals, branched aldehydes such as isobutyraldehyde, 2-methylbutanal, 3-methylbutanal, 3,3-dimethylbutanal, 2-methylpentanal, 2-ethylhexanal and 2-methyldecanal are used.

Suitable ketones for the ketals used are for example the following compounds: methyl ethyl ketone, diethyl ketone, methyl isopropyl ketone, diisopropyl ketone, diisobutyl ketone, methyl isobutyl ketone, methoxyacetone, cyclopentanone, cyclohexanone, methylcyclopentanones, methylcyclohexanones, cyclohexenone, acetophenone and substituted acetophenones.

The catalysts used for the novel process of preparing vinyl ethers are phophates having a zeolite structure and/or precipitated phosphates of the elements B, Zr, Ce or Fe and/or phosphoric acid or boric acid on carrier materials and/or acidic undoped metal oxides in general, more particularly for example aluminum phosphates, silicon aluminum phosphates, silicon iron aluminum phosphates, cobalt aluminum phosphate, iron aluminum phosphate, boron aluminum phosphates of zeolite structure, cerium phosphates, zirconium phosphates, boron phosphates, iron phosphates or mixtures thereof.

The aluminum phosphate catalysts used are in particular aluminum phosphates synthesized under hydrothermal conditions. These aluminum phosphates have a zeolite structure.

Suitable aluminum phosphates prepared under hydrothermal conditions are for example APO-5, APO-9, APO-11, APO-12, APO-14, APO-21, APO-25, APO-31 and APO-33. Syntheses of these compounds are described in EP 132,708, U.S. Pat. No. 4,310,440 and U.S. Pat. No. 4,473,663.

$AlPO_4$-5 (APO-5), for example, is synthesized by mixing orthophosphoric acid with pseudoboehmite (Catapal SB) in water to give a homogeneous mixture, adding tetrapropylammonium hydroxide to the mixture, and then reacting the mixture at about 150° C. for from 20 to 60 hours under autogenous pressure in an autoclave. The AlPO$_4$ produced by filtration is dried at from 100° to 160° C. and calcined at from 450° to 550° C.

AlPO$_4$-9 (APO-9) is likewise synthesized from orthophosphoric acid and pseudoboehmite, but in aqueous DABCO solution (1,4-diazabicyclo[2.2.2]octane) at about 200° C. under autogenous pressure in the course of from 200 to 400 hours.

The synthesis of AlPO$_4$-21 (APO-21) is effected from orthophosphoric acid and pseudoboehmite in aqueous pyrrolidone solution at from 150° to 200° C. under autogenous pressure in the course of from 50 to 200 hours.

According to the invention, it is also possible to use silicon aluminum phosphates, for example SAPO-5, SAPO-11, SAPO-31 and SAPO-34. The synthesis of these compounds is described in EP 103,117 and U.S. Pat. No. 4,440,871. These silicon aluminum phosphates have a zeolite structure. SAPOs are prepared by crystallization from aqueous mixture at from 100° to 250° C. under autogenous pressure in the course of from 2 hours to 2 weeks, the reaction mixture comprising a silicon, aluminum and phosphorus component being reacted in aqueous organoamine solution. These silicon aluminum phosphates have a zeolite structure.

SAPO-5 is obtained for example by mixing SiO$_2$, suspended in aqueous tetrapropylammonium hydroxide solution, with an aqueous suspension of pseudoboehmite and orthophosphoric acid and subsequent reaction at from 150° to 200° C. for from 20 to 200 hours under autogenous pressure in a stirred autoclave. After filtration the powder is dried at from 110° to 168° C. and calcined at from 450° to 550° C.

Suitable silicon aluminum phosphates also include for example ZYT-5, ZYT-6, ZYT-7, ZYT-9, ZYT-11 and ZYT-12.

The phosphates thus prepared and after they have been isolated, dried at from 100° to 160° C., preferably at from 110° C. and calcined at from 450° to 550° C., preferably at 500° C., can be molded with a binder in a ratio of from 90:10 to 40:60% by weight into extrudates or tablets. Binders are various aluminum oxides, preferably boehmite, amorphous aluminosilicates having an SiO$_2$/Al$_2$O$_3$ ratio of from 25:75 to 90:5, preferably 75:25, silicon dioxide, preferably finely divided SiO$_2$, mixtures of finely divided SiO$_2$ and finely divided Al$_2$O$_3$ and also clay. After molding the extrudates or pellets are dried at 110° C./16 h and calcined at 500° C./16 h.

Advantageous catalysts are also obtained when the isolated phosphate is molded directly after drying and not subjected to a calcination until after molding. The phosphates prepared can be used in pure form, without binder, as extrudates or tablets, in which case extruding or peptization aids, for example ethylcellulose, stearic acid, potato starch, formic acid, oxalic acid, acetic acid, nitric acid, ammonia, amines, silicoesters and graphite or mixtures thereof are used.

If the phosphate, for example silicon aluminum phosphate, owing to its manner of preparation, is present not in the catalytically active acidic H form but for example in the Na form, then it can be completely or partially converted into the desired H form by ion exchange, for example with ammonium ions and subsequent calcination or by treatment with acids.

Suitable phosphate catalysts also include precipitated aluminum phosphates of B, Fe, Zr, Ce and mixtures thereof.

Boron phosphates for use as catalysts for the process according to the invention can be prepared for example by mixing and kneading concentrated boric acid and phosphoric acid and subsequent drying and calcination in an inert gas, air or steam atmosphere at from 258° to 650° C., preferably at from 300° to 500° C.

If in the course of using the phosphate catalysts according to the invention they become deactivated due to coking it is advisable to regenerate the phosphate catalysts by burning off the coke deposit with air or with an air/N$_2$ mixture at from 400° to 550° C.

By partial precoking it is possible to adjust the activity of the catalyst to optimum selectivity in respect of the desired reaction product.

To obtain a high selectivity, a high conversion and long times on stream, it can be advantageous to modify the phosphate catalysts. A suitable form of modification of the catalysts comprises for example doping the molded or unmolded phosphate with metal salts by ion exchange or by impregnation. The metals used are metals of the 3rd, 4th and 5th main group such as Al, Ga, Ge, Sn, Pb or Ni, transition metals of the 4th to 8th subgroups such as Ti, Zr, V, Nb, Cr, Mo, W, Mn, Re, Fe, Ru, Os, Co, Rh, Ir, Ni, Pd or Pt, transition metals of the 1st and 2nd subgroups such as Cu, Ag, or Zn, or rare earth metals such as La, Ce, Pr, Nd, Er, Yb and U.

Advantageously, the doping is carried out by introducing the molded phosphate into a riser pipe and passing an aqueous or ammoniacal solution of a halide or nitrate of the above-described metals over it at from 20° to 100° C. (ion exchange). A further way of applying the metal comprises impregnating the phosphate with a halide, a nitrate or an oxide of the above-described metals in aqueous, alcoholic or ammoniacal solution. Both ion exchange and impregnation are followed by at least one drying step, alternatively by a further calcination.

A possible embodiment comprises dissolving Cu(NO$_3$)$_2$×H$_2$O or Ni(NO$_3$)$_2$×6 H$_2$O or Ce(NO$_3$)$_3$×6 H$_2$O or La(NO$_3$)$_2$×6 H$_2$O or Cs$_2$CO$_3$ in water. This solution is used to saturate the molded or unmolded phosphate for a certain period, say 30 minutes. Any supernatant solution is stripped of water in a rotary evaporator. The saturated phosphate is then dried at about 150° C. and calcined at about 550° C. This process of saturation may be repeated several times in succession in order to establish the desired metal content.

It is also possible to prepare an aqueous Ni(CO$_3$)$_2$ solution or ammoniacal Pd(CO$_3$)$_2$ solution and to suspend the pure pulverulent phosphate therein at from 40° to 100° C. by stirring for about 24 hours. After removal by filtration, drying at about 150° C. and calcination at about 500° C. the phosphate catalyst thus obtained can be further processed with or without binders into extrudates, pellets or fluidizable material.

A further modifying technique comprises subjecting the phosphate, in molded or unmolded form, to a treatment with acids such as hydrochloric acid, hydrofluoric acid and/or steam. This is advantageously done by treating the phosphate, before or after it has been molded with binder, with a from 3 to 25% strength by weight, in particular from 12 to 20% strength by weight, aqueous hydrochloric acid at from 60° to 80° C. for from 1 to 3 hours. The phosphate thus treated is then washed with water, dried and calcined at from 400° to 500° C.

A particular embodiment for the acid treatment comprises treating the phosphate before it is molded at elevated temperature with hydrofluoric acid, generally used in the form of from 0.001N to 2N, preferably from 0.05N to 0.5N, hydrofluoric acid, for example by refluxing for from 0.5 to 5, preferably from 1 to 3, hours. After isolation, for example by filtration and washing, the phosphate is advantageously dried at from 100° to 160° C. and calcined at from 450° to 600° C. In a further preferred embodiment for the acid treatment, the phosphate, after molding with binders, is treated at elevated temperatures with from 12 to 20% strength by weight hydrochloric acid advantageously at from 50° to 90° C., in particular at from 60° to 80° C., for from 0.5 to 5 hours. The phosphate is then washed and advantageously dried at from 100° to 160° C. and calcined at from 450° to 600° C. The HF treatment may also be followed by an HCl treatment.

Suitable catalysts also include the acidic undoped oxides of elements of main groups III and IV and also of subgroups IV to VI of the periodic table, in particular oxides such as silicon dioxide in the form of silica gel, diatomaceous earth, and also titanium dioxide, zirconium dioxide, phosphorus oxides, vanadium oxides, niobium oxides, boron oxides, aluminum oxides, chromium oxides, iron oxides, molybdenum oxides, tungsten oxides or pumice or mixtures thereof. The treatment with acids as described above is a possible way of obtaining modification.

It is also possible to use catalysts impregnated with phosphoric acid or boric acid. Phosphoric acid or boric acid is applied to $SiO_2$, $Al_2O_3$ or pumice carriers or other acidic metal oxides as carrier material, for example by impregnating or spraying. A catalyst containing phosphoric acid may be obtained for example by impregnating $SiO_2$ with $H_3PO_4$ and then drying and/or calcining. However, phosphoric acid can also be sprayed together with silica gel in a spray tower; this is followed by drying and usually calcination. Phosphoric acid can also be sprayed onto the carrier material in an impregnating mill.

The catalysts described here may optionally be used as from 2- to 4-mm extrudates or as tablets from 3 to 5 mm diameter or as chips from 0.1 to 0.5 mm in particle size or in fluidizable form.

The process according to the invention is carried out under the following reaction conditions:

The reaction is advantageously carried out in the gas phase at from 100° to 500° C., in particular at from 150° to 350° C., under a pressure of from 0.1 to 100 bar, in particular under from 0.5 to 10 bar. In the gas phase, the catalyst is advantageously run at a weight hourly space velocity (WHSV) of from 0.1 to 20, in particular from 1 to 10, g of starting material of the formula II per g of catalyst per hour. The reaction in the gas phase can be carried out in a fixed bed or in a fluidized bed. It is also possible to carry out the reaction in the liquid phase (as suspension, trickle bed or liquid phase procedure) at from 50° to 200° C. The reaction may be carried out batchwise but is preferably carried out continuously. Reduced pressure can be particularly advantageous.

Sparingly volatile or solid starting materials are used in dissolved form, for example in THF, toluene or petroleum ether solution. In general, the starting material may be diluted with such solvents or with inert gases such as $N_2$, Ar or $H_2O$ vapor.

After the reaction, the products formed are isolated in a conventional manner, for example by distillation from the reaction mixture; unconverted starting materials may be recycled into the reaction.

A particular advantage is obtained if the gaseous reaction products are immediately introduced into the separation stage and then split into their individual components. Such a separation may be carried out for example in a fractionating column. It is a preferred embodiment to cool the reaction outputs in an aqueous hydrogen carbonate solution, for example $KHCO_3$ or $NaHCO_3/Na_2SO_4$.

EXAMPLES 1 to 15

The reactions in the gas phase are carried out under isothermal conditions in a tubular reactor (coil, internal diameter 0.6 cm, length 90 cm) for not less than 6 hours. The reaction products are cooled down, separated and characterized in a conventional manner. The quantitative determination of the reaction products and starting materials was effected by gas chromatography in a conventional manner.

The catalysts used for the process according to the invention are:

CATALYST A $AlPO_4$-5 (APO-5) is synthesized by dissolving and suspending 200 g of 98% strength phosphoric acid and 136 g of boehmite in 335 g of water, adding 678 g of a 30% strength aqueous tetrapropylammonium hydroxide solution, and reacting this mixture in a stirred autoclave under autogenous pressure at 150° C. for 43 hours. After filtration the crystalline material is dried at 120° C. and calcined at 500° C./16 h. The $AlPO_4$-5 thus synthesized contains 45.5% by weight of $Al_2O_3$ and 46.5% by weight of $P_2O_5$. This material is molded with pseudoboehmite in a weight ratio of 60:40 into 2-mm extrudates, dried again at 120° C. and calcined at 500° C./16 h.

CATALYST B $AlPO_4$-12 (APO-12) is synthesized by dissolving and suspending 200 g of 98% strength phosphoric acid and 136 g of boehmite in 400 g of water, adding an aqueous solution of 60 g of ethylenediamine and 320 g of $H_2O$ and reacting this mixture in a stirred autoclave under autogenous pressure at 200° C. for 24 hours. After filtration the crystalline material is dried at 120° C. and calcined at 500° C./16 h. The $AlPO_4$-12 thus synthesized contains 55.5% by weight of $P_2O_5$ and 39.7% by weight of $Al_2O_3$. This material is molded with extrusion aids into 3-mm extrudates, dried again at 120° C. and calcined at 500° C./6 h.

CATALYST C

Silicon aluminum phosphate-5 (SAPO-5) is prepared from a mixture of 200 g of 98% strength phosphoric acid, 136 g of boehmite, 60 g of silicasol (30% strength), 287 g of tripropylamine and 587 g of $H_2O$. This mixture is reacted at 150° C. under autogenous pressure for 168 hours. After filtration the crystalline product is dried at 120° C. and calcined at 500° C./16 h. SAPO-5 contains 49.8% by weight of $P_2O_5$, 33.0% by weight of $Al_2O_3$ and 6.2% by weight of $SiO_2$. SAPO-5 is molded with an extrusion aid to 3-mm extrudates, dried again at 120° C. and calcined at 500° C.

CATALYST D

BPO₄ is prepared by adding together 49 g of H₃BO₃ and 117 g of H₃PO₄ (75% strength) in a kneader, evaporating off excess water and molding the reaction product into 3-mm extrudates. These extrudates are dried at 100° C. and calcined at 350° C. Catalyst D contains 8.77% by weight of B and 28.3% by weight of P.

CATALYST E

CePO₄ is obtained by precipitation from 52 g of Ce(NO₃)₃×6 H₂O and 56 g of NaH₂PO₄×2 H₂O. After filtration the material is molded into extrudates, dried at 120° C. and calcined at 450° C. Catalyst E contains 17.1% by weight of Ce and 12.7% by weight of P.

CATALYST F

Commercial zirconium phosphate (CZP 100®) is molded with molding aids into 2-mm extrudates, dried at 110° C. and calcined at 500° C./16 h.

CATALYST G

SiO₂ commercially available as D 11-10®.

CATALYST H 100 g of SiO₂ extrudates (D 11-10) are refluxed with 280 ml of 0.1N HF and 80 ml of H₂O for 1 hour. The material is then washed neutral, dried at 110° C. and calcined at 500° C./5 h.

CATALYST I

D 10-10 Al₂O₃ is impregnated with H₃BO₃, dried at 110° C. and calcined at 500° C./5 h. Catalyst I is composed of 85% of Al₂O₃ and 15% of B₂O₃.

CATALYST J

Catalyst J is obtained by treating D 10-10 Al₂O₃ with 85% strength H₃PO₄ for 30 minutes, then drying at 130° C./2 h and then calcining at 540° C./2 h. The P content is 4.9% by weight.

CATALYST K

TiO₂ P 25® is molded into 2-mm extrudates, dried at 110° C. and calcined at 500° C./16 h.

CATALYST L 200 g of catalyst G are treated with 600 ml of 15% strength HCL at 80° C./1 h. The material is then washed until Cl-free, dried at 110° C. and calcined at 600° C./1 h.

The experimental results and the reaction conditions are listed in the Table below.

| Reaction (A) | 1,1-Dimethoxyethane → methyl vinyl ether + methanol |
|---|---|
| Reaction (B) | 1,1-Dimethoxy-2-methylpropane → 1-methoxy-2-methyl-prop-1-ene + methanol |
| Reaction (C) | 1,1-i-Propoxybutane diluted 75:25 with THF → 1-i-propoxybut-1-ene + isopropanol |
| Reaction (D) | 1,1-Dimethoxyoctane diluted 75:25 with THF → 1-dimethoxyoct-1-ene + methanol |
| Reaction (E) | 1,1-Dimethoxy-2-phenylethane diluted 50:50 with THF → 1-methoxystyrene + methanol |
| Reaction (F) | 1,1-Dimethoxy-2-[p-fluorophenyl]ethane diluted 50:50 with THF → 1-methoxy-p-fluorostyrene + methanol |
| Reaction (G) | Hexyldimethoxymethane diluted 50:50 with THF → cyclohexanemethylene methyl ether + methanol |
| Reaction (H) | Cyclohexanone diethyl ketal diluted 50:50 with THF → cyclohexenyl ethyl ether + ethanol |

Dilution indication in % by weight.

TABLE 1

| | Example | | | | | | | | |
|---|---|---|---|---|---|---|---|---|---|
| | 1 | 2 | 3 | 4 | 5 | 6 | 7 | 8 | 9 |
| Reaction | A) | A) | A) | A) | A) | A) | A) | A) | A) |
| Catalyst | A | C | C | D | E | F | H | I | K |
| Temperature °C. | 350 | 300 | 350 | 300 | 300 | 320 | 300 | 320 | 320 |
| WHSV h⁻¹ | 2 | 2 | 3.5 | 2 | 2 | 2 | 2 | 2 | 2 |
| Conversion % | 90.3 | 100 | 100 | 100 | 95.8 | 87.9 | 100 | 94.7 | 97.3 |
| Selectivity % | 84.7 | 97.3 | 93.8 | 95.4 | 90.3 | 85.2 | 88.7 | 86.9 | 89.5 |

TABLE 2

| | Example | | | | | | | | |
|---|---|---|---|---|---|---|---|---|---|
| | 10 | 11 | 12 | 13 | 14 | 15 | 16 | 17 | 18 |
| Reaction | B) | B) | C) | C) | D) | E) | E) | E) | E) |
| Catalyst | C | D | D | E | C | B | C | D | E |
| Temperature °C. | 300 | 300 | 300 | 300 | 300 | 300 | 300 | 300 | 300 |
| WHSV h⁻¹ | 2 | 2 | 2 | 2 | 2 | 2 | 2 | 2 | 2 |
| Conversion % | 100 | 100 | 100 | 98.4 | 100 | 92.7 | 100 | 100 | 100 |
| Selectivity % | 94.1 | 92.7 | 93.5 | 87.6 | 94.0 | 87.7 | 91.8 | 90.5 | 89.3 |

TABLE 3

| | Example | | | | | | | |
|---|---|---|---|---|---|---|---|---|
| | 19 | 20 | 21 | 22 | 23 | 24 | 25 | 26 |
| Reaction | E) | E) | E) | E) | F) | G) | G) | H) |
| Catalyst | E | J | L | K | D | C | D | D |
| Temperature °C. | 300 | 300 | 300 | 300 | 300 | 300 | 300 | 300 |
| WHSV h⁻¹ | 2 | 2 | 2 | 2 | 2 | 2 | 2 | 2 |
| Conversion % | 97.9 | 95.9 | 100 | 98.4 | 100 | 100 | 100 | 100 |
| Selectivity % | 80.6 | 86.1 | 88.2 | 90.2 | 92.3 | 83.2 | 84.3 | 87.9 |

We claim:

1. A process for preparing a vinyl ether of the formula (I)

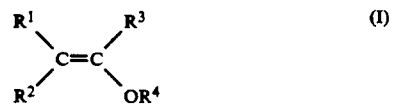

where R¹, R² and R³ are identical to or different from one another, each being hydrogen, straight-chain or branched alkyl or alkenyl of up to 12 carbon atoms, cycloalkyl or cycloalkylene of from 5 to 8 carbon atoms, aryl, alkylaryl, aralkyl and aralkenyl of from 6 to 16 carbon atoms, halogen-substituted aryl or a tetrahydrofuran, dihydrothiopene, thiophene, pyridine or thiopyran radical and in addition the radicals $R^1$ and $R^2$ or $R^1$ and $R^3$, together with the carbon atom to which they are bonded, can form a cycloalkane, cycloalkene, or a tetrahydrofuran, dihydrothiopene, thiophene, pyridine or thiopyran radical and $R^4$ is alkyl, alkylaryl or aralkyl, which comprises eliminating an alcohol from an acetal/ketal of the formula (II)

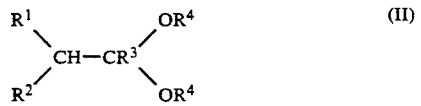

where $R^1$, $R^2$, $R^3$ and $R^4$ are each as defined above, in the presence of an acidic catalyst, said catalyst being selected from the group consisting of aluminum phosphates, silicon aluminum phosphates, silicon iron aluminum phosphates, iron aluminum phosphates, boron aluminum phosphates, cobalt aluminum phosphates, and mixtures thereof, all of the above phosphates being of zeolite structure, a $SiO_2$, $Al_2O_3$ or pumice carrier impregnated with phosphoric acid or boric acid, silicon dioxide, titanium oxide, zirconium dioxide, phosphorus oxides, niobium oxides, boron oxides, aluminum oxides, chromium oxides, iron oxides, molybdenum oxides, tungsten oxides, pumice and mixtures thereof.

2. The process of claim 1, wherein the catalyst is a hydrothermally prepared aluminum phosphate, silicon aluminum phosphate, silicon iron aluminum phosphate, iron aluminum phosphate, boron aluminum phosphate, cobalt aluminum phosphate or a mixture thereof.

3. The process of claim 1, wherein the reaction is carried out in the gas phase.

4. The process of claim 3, wherein the catalyst is run at a weight hourly space velocity of from 0.1 g to 20 g of starting material of the formula II per g of catalyst per hour.

* * * * *

UNITED STATES PATENT AND TRADEMARK OFFICE
CERTIFICATE OF CORRECTION

PATENT NO. : 5,130,435

DATED : July 14, 1992

INVENTOR(S) : Wolfgang HOELDERICH et al.

It is certified that error appears in the above-identified patent and that said Letters Patent is hereby corrected as shown below:

Claim 1, column 9, line 8: "dihydrothiopene" should read -- dihydrothiophene --

Signed and Sealed this

Seventeenth Day of August, 1993

Attest:

BRUCE LEHMAN

Attesting Officer

Commissioner of Patents and Trademarks